United States Patent [19]

Fitzi

[11] 3,940,486

[45] Feb. 24, 1976

[54] IMIDAZOLE DERIVATIVES IN THE TREATMENT OF PAIN

[75] Inventor: Konrad Fitzi, Neuallschwil, Switzerland

[73] Assignee: Ciba-Geigy Corporation, Ardsley, N.Y.

[22] Filed: Apr. 18, 1974

[21] Appl. No.: 461,824

Related U.S. Application Data

[62] Division of Ser. No. 247,431, April 25, 1972, abandoned.

[30] Foreign Application Priority Data

May 11, 1971 Switzerland.......................... 6967/71
Mar. 22, 1972 Switzerland.......................... 4250/72

[52] U.S. Cl....... 424/263; 260/250 R; 260/294.8 R; 260/294.8 G; 260/295 S; 260/296 R; 260/297 R; 424/250; 424/266

[51] Int. Cl.²......................................... A61K 27/00

[58] Field of Search......... 424/273, 263; 260/296 R, 260/294.8 F, 294.8 G, 295 S

[56] References Cited

UNITED STATES PATENTS 3,707,475   12/1972   Lombardino ...................... 260/309

Primary Examiner—Stanley J. Friedman
Attorney, Agent, or Firm—Joseph G. Kolodny; John J. Maitner; Theodore O. Groeger

[57] ABSTRACT

Compounds of the formula

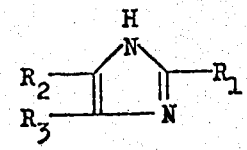

wherein $R_1$ represents lower alkyl, cycloalkyl or phenyl which is optionally substituted by halogen, lower alkyl or lower alkoxy, and one of the groups $R_2$ and $R_3$ represents phenyl which is optionally substituted by halogen, lower alkyl, hydroxy, lower alkoxy, lower alkylthio or lower alkylsulphonyl, and the other represents a 6-membered heteroaromatic radical containing 1 or 2 ring nitrogen atoms, their N-oxides and salts, with anti-inflammatory, antinociceptive and antipyretic activity, they are active ingredients of pharmaceutical compositions and can be used for the relief and removal of pain as well as for the treatment of rheumatic, arthritic and other inflammatory complaints; an illustrative example is 2-isopropyl-4(5)-(p-methoxyphenyl)-5(4)-3-pyridyl-imidazole.

2 Claims, No Drawings

IMIDAZOLE DERIVATIVES IN THE TREATMENT OF PAIN

CROSS-REFERENCE TO RELATED APPLICATION

This application is a division of application Ser. No. 247,431, filed on Apr. 25, 1972, now abandoned.

The present invention relates to new imidazole derivatives which possess valuable pharmacological properties, processes for their manufacture, pharmaceutical preparations which contain the new imidazoles, and their use.

In particular, the invention relates to imidazole derivatives of the general formula

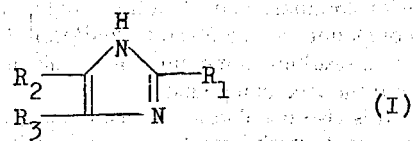

wherein $R_1$ represents lower alkyl, cycloalkyl or phenyl which is optionally substituted by halogen, lower alkyl or lower alkoxy, and one of the groups $R_2$ and $R_3$ represents phenyl which is optionally substituted by halogen, lower alkyl, hydroxy, lower alkoxy, lower alkythio or lower alkylsulphonyl, and the other represents a 6-membered heteroaromatic radical containing 1 or 2 ring nitrogen atoms, and N-oxides thereof and salts of such compounds.

The compounds of the present invention possess valuable pharmacological properties, in particular antiflammatory, antinociceptive, and antipyretic action with favourable therapeutic index.

The antiphlogistic action of the new imidazole derivatives when administered orally is shown, for example, in the Bolus alba oedema test on rats according to G. Wilhelmi, Jap. J. Pharmacol, 15, 187 (1965).

The analgesic action of the new imidazole derivatives is demonstrated, for example, in mice according to the method described by E. Siegmund, R. Cadmus and G. Lu, Proc. Soc. Exp. Biol. Med. 95, 729 (1957). In this method, the amount of substance is determined which is necessary to prevent the syndrome caused by the intraperitoneal injection of 2-phenyl-1,4-benzoquinone.

To determine the antipyretic action, the new compounds are administered perorally in suitable doses to rats which had been injected intramuscularly 16–18 hours previously with a suspension of 15% baker's yeast with 1% tragacanth and 1% sodium chloride in distilled water in an amount of 1 ml per 100 g body weight. The feverish temperatures induced by the yeast are taken rectally 1 hour and half an hour before the test substances are administered, and half-hourly at an interval of half an hour to 5 hours after the administration of the test substances. The maximum drop in temperature as well as the arithmetic average temperature fall during the 5 hours after the administration of the test substances are determined as basis of comparison contrasted with the average of the two measurements taken before the administration.

The new imidazole derivatives are suitable as active substances which may be administered orally, rectally or parentally for the alleviation and relief of pains of varying origin, as well as for the treatment of reumatic, arthritic and other inflammatory complaints.

In the imidazole derivatives of the general formula I and the corresponding starting materials which are further cited hereinbelow, a lower alkyl radical $R_1$ contains in particular up to 6 carbon atoms and is primarily a branched alkyl radical or a cycloalkyl radical, preferably containing up to 6 carbon atoms, chiefly isopropyl or sec.butyl or preferably tert.butyl, also cyclopropyl. The substituent $R_1$ as a phenyl radical which is optionally substituted, in particular monosubstituted, by halogen, for example fluorine, chlorine or bromine, lower alkyl, for example methyl or ethyl, or lower alkoxy, for example methoxy or ethoxy, represents a phenyl radical which is correspondingly substituted in the p-position, the halogen substituent being preferably a chlorine atom.

A substituted phenyl radical $R_2$ or $R_3$ is preferably monosubstituted and may contain a substituent in the o-, m- or p-position. As substituents there may be cited chiefly: chlorine, methyl, hydroxy, methoxy, ethoxy, methylthio, ethylthio, methylsulphonyl or ethylsulphonyl.

A monoazocyclic radical $R_2$ or $R_3$ is pyridyl, for example 2-, 3- or 4-pyridyl, while a diazacyclic radical $R_2$ or $R_3$ stands preferably for pyrazinyl.

Particularly valuable compounds are those of the formula I, wherein $R_1$ represents lower alkyl containing up to 6 carbon atoms, preferably branched lower alkyl containing 3 and, in particular, 4 carbon atoms, or represents phenyl which is optionally monosubstituted by methyl, methoxy or chlorine, and one of the radicals $R_2$ and $R_3$ represents phenyl which is optionally substituted by methyl, methoxy or chlorine and the other represents pyridyl, such as 2-pyridyl or 4-pyridyl, but especially 3-pyridyl, and acid addition salts thereof.

As examples of pharmacologically valuable compounds of the kind indicated hereinabove particular mention may be made of the following:
2-tert.-butyl-4(5)-phenyl-5(4)-(3-pyridyl)-imidazole, and 2-tert.-butyl-4(5)-(p-methoxyphenyl)-5(4)-(3-pyridyl)-imidazole, 2-(p-chlorophenyl)-4(5)-(p-methoxyphenyl)-5(4)-(3-pyridyl)-imidazole, 2-tert.-butyl-4(5)-(m-methylphenyl)-5(4)-(3-pyridyl)-imidazole and 2-(p-chlorophenyl)-4(5)-phenyl-5(4)-(3-pyridyl)-imidazole, also 2-(p-chlorophenyl)-4(5)-(p-methoxyphenyl)-5(4)-(2-pyridyl)-imidazole, 2-tert.-butyl-4(5)-(p-methoxyphenyl)-5(4)-(4-pyridyl)-imidazole,2-tert.butyl-4(5)-phenyl-5(4)-(4-pyridyl)-imidazole and 2-(p-chlorophenyl)-4(5)-(p-methoxyphenyl)-5(4)-(4-pyridyl)-imidazole, and their salts, in particular the pharmaceutically tolerable acid addition salts.

The new compounds can be manufactured in known manner. Thus, for example, it is possible to react a substituted diketone of the general formula

a corresponding mono-oxime or N-oxide, with ammonia and an aldehyde of the general formula $R_1$—CHO (III), and, if desired, to convert a resulting compound into an N-oxide, or a resulting N-oxide into the free compound, and/or, if desired, to convert a resulting compound into a salt or a resulting salt into the free compound.

In the above reaction, the ammonia (also in the form of an agent which liberates ammonia) is used preferably in excess, with at least the dimolar amount being used in the case of a diketone and, in the case of the corresponding mono-oxime, which leads to the formation of an N-oxide of a compound of the formula I, at least the equimolar amount being used.

An agent which liberates ammonia is, for example, an ammonia salt of an organic carboxylic acid, such as an ammonium-lower alkanoate, preferably ammonium acetate, also ammonium formiate, in addition a suitable carboxylic amide, in particular of formic acid, for example formamide. An ammonium salt is usually used in substantial excess and in the presence of an acid, such as a lower alkanecarboxylic acid, for example formic or acetic acid or of another acid of the formula $R_1—C(=O)—OH$ (IV), wherein $R_1$ is preferably a radical of aliphatic character, it being possible to use such an acid simultaneously as solvent. It is also possible to use formamide simultaneously as solvent, preferably in excess, for example in a 5–25-fold excess. The reaction can be carried out in the presence of an additional solvent, thus formamide, for example, in the presence of dimethyl formamide, preferably at elevated temperature, for example at the boiling temperature of the reaction mixture, on using formamide at about 180°C to about 200°C (at which temperature the formamide decomposes), and, if desired, in a sealed vessel, optionally under pressure and/or in an inert gas atmosphere, for example in an atmosphere of nitrogen.

In the above process it is also possible to use the diketone of the formula II in the form of a compound which can be converted into the former, for example by carrying out the above reaction with an α-hydroxyketone of the formula

or with a mono-oxime derivative thereof, and in the presence of an oxidant conventionally used for the conversion into the diketone of the formula II, for example an oxidising heavy metal salt, preferably an organic copper-(II) salt, such as copper-(II)-acetate or copper-(II)-citrate, with the resulting imidazole derivative of the general formula I usually occuring in the form of a copper salt. The reaction is customarily carried out as described hereinabove, i.e. the ammonia or agent which liberates ammonia is used preferably in substantial excess, and the oxidation and simultaneous condensation is carried out, for example, in a lower alkanol, such as methanol or ethanol, preferably at elevated temperature, for example at about 30°C to about 100°C. The free imidazole derivative can be liberated from an occurring copper salt in conventional manner, for example by reaction with hydrogen sulphide in a lower alkanol and with the application of heat.

The diketones of the formula II or α-hydroxy ketones of the formula IIa are known or can be manufactured in a manner known per se. It is possible to obtain monooximes of compounds of the formula II, for example, by reacting a $R_3$- carboxylic ester, wherein $R_3$ represents the heterocyclic radical $R_2$ or $R_3$, such as a corresponding lower alkyl ester, for example ethyl ester, or optionally an N-oxide thereof, with an $R_2$- acetic acid ester, such as a lower alkyl ester, for example ethyl ester, in known manner to give the corresponding ketone of the formula

and reacting this latter with nitrous acid in an alcoholic solvent.

The new compound of the general formula I and their salts can also be manufactured, for example, by treating an amide of the general formula

with ammonia and, if desired, converting a resulting compound into an N-oxide, and/or, if desired, converting a resulting compound into a salt or a resulting salt into the free compound.

It is also possible to use the ammonia in the form of an agent which liberates ammonia, there being used as such, for example, the ammonia salts of carboxylic acids of the formula IV cited hereinabove, in particular the ammonium salt of a lower alkanecarboxylic acid, such as ammonium acetate, also formamide, usually in the presence of a lower alkanecarboxylic acid, for example acetic or formic acid. The reaction is carried out preferably at elevated temperature.

The starting materials of the general formula V can be manufactured, for example, by acylating 2-amino-1-oxo-1-$R_2$-2-$R_3$-ethane with halides, such as chlorides, of carboxylic acids of the formula IV or with corresponding anhydrides.

It is also possible to obtain the new imidazole derivatives of the general formula I and their salts by reacting a reactive ester of an α-hydroxy-ketone of the general formula IIa with an amidine of the general formula

or with a salt thereof, and, if desired, converting a resulting copound into an N-oxide, and/or, if desired, converting a resulting compound into a salt or a resulting salt into the free compound.

A reactive ester is, for example, a corresponding ester of a hydrohalic acid, in particular the corresponding chloride or bromide, also of a strong organic sulphonic acid, such as a lower alkanesulphonic or arenesulphonic acid, for example methane- or p-toluenesulphonic acid. The condensation can be carried out usually by heating the reactants in an inert solvent, such as a halogenated aliphatic hydrocarbon, for example chloroform, at moderately elevated temperature, if necessary in the presence of a suitable condensation agent, such as a base.

Salts of amidines of the formula VI are, for example, their more stable hydrochlorides, which before use are converted preferably into the free amidines, for example by carrying out to the reaction with advantage in a two-phase system consisting of a solution of a reactive ester of an α-hydroxy-ketone of the general formula IIa in an inert organic solvent, for example chloroform, and an aqueous solution of the salt, for example the hydrochloride, of the amidine of the general formula VI. While heating and stirring vigorously, a dilute aqueous solution of an alkali metal hydroxide, for example potassium hydroxide or sodium hydroxide, is added dropwise in dimolar amount in order, on the one hand, to liberate the amidine, and on the other, to bind the acid which becomes liberated on the ring closure.

The compounds of the general formula I can also be obtained likewise reacting an oxazole of the general formula

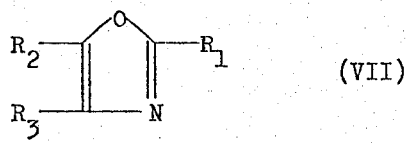 (VII)

with ammonia, and if desired, converting a resulting compound into an oxide, and/or, if desired, converting a resulting compound into a salt or a resulting salt into the free compound.

The ammonia may be used in the form of an agent which liberates ammonia, for example, formamide optionally together with ammonia. It is possible, for example, to heat an oxazole of the formula VII with a mixture of liquid ammonia and formamide in an autoclave to temperatures of about 180°C to about 220°C, or a mixture of the above mentioned oxazole with formamide to the boiling or decomposition temperature of the formamide.

The new oxazoles of the general formula VII which are used as starting materials can be manufactured, for example, by reacting α-hydroxy-ketones of the general formula IIa with halides, for example chlorides, of carboxylic acids of the formula IV or corresponding anhydrides to form the corresponding esters. The latter are reacted with an ammonium salt of a lower alkane acid while heating; for example, they are boiled with excess ammonium acetate in glacial acetic acid under reflux, in the process of which the desired oxazole is formed.

According to a further process, the oxazoles of the general formula VII are obtained by dehydrating an amide of the general formula V, for example by boiling with thionyl chloride under reflux in the presence, or absence, of an inert solvent, for example benzene, until the evolution of hydrogen chloride has ceased, or by treatment with concentrated sulphuric acid at temperatures of about 0°C to room temperature.

The above oxazoles of the general formula VII can likewise be obtained by reacting a nitrile of the formula $R_1$—CN (VIII) with a compound of the general formula IIa, in the presence of a mineral acid. For example, an equimolar mixture of the cited starting materials is treated with concentrated sulphuric acid at temperatures between 0° and 30°C, or with polyphosphoric acid at about 80°C to 120°C.

The oxazoles of the general formula VII can likewise be obtained by condensing reactive esters, in particular those of hydrohalic acids, of compounds of the general formula IIa, with amides of the formula

 $R_1$—C(=O)—NH$_2$ (IX)

preferably on heating to temperatures between about 130°C and about 170°C, or by reacting them with tin-IV-chloride complexes of carboxylic nitriles of the formula VIII at room temperature to about 100°C.

A resulting compound can be converted into an N-oxide in known manner, for example by treatment with an N-oxidising agent, such as hydrogen peroxide or a suitable peracid, such as a lower alkanepercarboxylic acid, for example peracetic acid, a benzenepercarboxylic acid, for example perbenzoic acid, 3-chloro-perbenzoic acid or monoperthalic acid, or an organic persulphonic acid.

A resulting N-oxide can be converted into a compound of the formula I by reduction, for example by treatment with hydrogen in the presence of a catalyst, such as Raney nickel, and using as solvent, for example, a lower alkanol, in particular methanol or ethanol, or with a reducing agent conventionally used for the reduction of N-oxides, for example lithium aluminium anhydride, phosphorus trichloride or sodium dithionite (sodium hyposulphite), the latter also in the form of a hydrate, for example a dihydrate.

The process also comprises those embodiments of the invention in which compounds occurring as intermediate products are used as starting material and the missing steps of the process are carried out, or the process is interrupted at any stage; starting materials can also be used in the form of derivatives or be formed during the reaction.

Preferred starting materials and reaction conditions are those which lead to the compounds cited at the outset as being especially preferred.

The compounds of the general formula I which are obtainable according to the process of the invention, and N-oxides thereof, may, if desired, be converted in conventional manner into their salts, for example into addition salts of inorganic and organic acids. Suitable acids are primarily those which, with the free compounds, form pharmaceutically tolerable non-toxic salts, for example hydrochloric acid, hydrobromic acid, sulphuric acid, phosphoric acid, methanesulphonic acid, ethanesulphonic acid, β-hydroxyethanesulphonic acid, acetic acid, malic acid, tartaric acid, citric acid, lactic acid, oxalic acid, succinic acid, fumaric acid, maleic acid, benzoic acid, salicyclic acid, phenylacetic acid, mandelic acid or embonic acid. The acid addition salts can be obtained in known manner, for example by treatment with an acid in the presence of a suitable solvent.

The new imidazole compounds of the general formula I and their N-oxides, as well as the pharmaceutically tolerable salts, such as the acid addition salts thereof, may be administered in the form of pharmaceutical preparations preferably enterally, for example perorally or rectally. The daily dose of the active substance is in the range between about 1 mg/kg and about 100 mg/kg. Suitable unit dose forms, such as coated tablets, tablets, suppositories or ampoules, contain the active substance preferably in an amount of 0.25 – 5 mg/kg body weight of the species to be treated.

Unit dose forms for the peroral administration contain preferably between 10–90% of active substance. To manufacture these, the active substance can be combined, for example, with solid carriers in powder form, such as carbohydrates, for example lactose, saccharose, sorbitol or mannitol; starches, such as potato starch, maize starch or amylopectin, also laminaria powder or citrus pulp powder, cellulose derivatives or gelatine, optionally with the addition of lubricants, such as magnesium or calcium stearate or polyethylene glycols, for the manufacture of tablets or coated tablet cores. The latter can be coated, for example, with concentrated sugar solutions which contain in addition, for example, gum arabic, talcum and/or titanium dioxide, or with a lacquer which is dissolved in readily volatile organic solvents or solvent mixtures. It is possible to add dyes to these coatings, for example to distinguish different doses of active substance. Further suitable oral unit dose forms are push-fit capsules of gelatine, and also soft, sealed capsules of gelatine and a plasticiser, such as glycerol. The former contain the active substance preferably in granule form in admixture with lubricants, such as talcum or magnesium stearate, and optionally stabilisers, such as sodium metabisulphite ($Na_2S_2O_5$) or ascorbic acid. In soft capsules, the active substance is preferably dissolved or suspended in suitable liquids, such as liquid polyethylene glycols, it being possible likewise to add stabilisers.

Suitable unit dose forms for rectal administration are, for example, suppositories, which consist of a combination of an active substance with a suppository base composition based on natural or synthetic triglycerides (for example cocoa butter), polyethylene glycols or suitable higher fatty alcohols, and gelatine rectal capsules which contain a combination of the active substance with polyethylene glycols.

Further application forms which may be cited are, for example, lotions, tinctures and ointments for percutaneous administration which are prepared with the conventional adjuvants.

The following directions will serve to illustrate the manufacture of a number of typical application forms in more detail:

a. 1000 g of 2-tert.butyl-4(5)-phenyl-5(4)-(3-pyridyl)-imidazole are mixed with 550 g of lactose and 292 g of potato starch, the mix is moistened with an alcoholic solution of 8 g of gelatine and granulated through a sieve. After the granules have been dried they are mixed with 60 g of potato starch, 60 g of talcum and 10 g of magnesium and 20 g of highly disperse silica and the mixture is pressed into 10,000 tablets each weighing 200 mg and containing 100 mg of active substance. If desired, the tablets may be provided with breaking notches to adjust the dosage more finely.

b. 100 g of 2-(p-chlorophenyl)-4(5)-(p-methoxyphenyl)-5(4)-(2-pyridyl)-imidazole are thoroughly mixed with 16 g of maize starch and 6 g of highly disperse silicium dioxide. The mixture is moistened with a solution of 2 g of stearic acid, 6 g of ethyl cellulose and 6 g of stearin in app. 70 ml of isopropanol and granulated through a sieve (Ph. Helv. V). The granules are dried for about 14 hours and then pressed through a sieve III–IIIa. They are subsequently mixed with 16 g of maize starch, 16 g of talcum and 2 g of magnesium stearate and pressed into 1000 coated tablet cores. These latter are coated with a concentrated syrup of 2 g of lac, 7.5 g of gum arabic, 0.15 g of dye, 2 g of highly disperse silicium dioxide, 25 g of talcum and 53. 35 g of sugar and dried. The resulting coated tablets each weight 260 mg and contain 100 mg of active substance.

c. 50 g of 2-tert.butyl-4(5)-p-methoxyphenyl)-5(4)-(4-pyridyl)-imidazole and 1950 g of finely ground suppository base composition (for example cocoa butter) are thoroughly mixed and then the mix is melted. From the melt, which is kept homogeneous by stirring, 1000 suppositories each weighing 2 g are cast. They each contain 50 mg of active substance.

d. 60 g of polyoxyethylene anhydrosorbitol monostearate, 30 g of anhydrosorbitol monostearate, 150 g of paraffin oil and 120 g of stearyl alcohol are melted together; then 50 g of 2-tert.butyl-4(5)-phenyl-5(4)-(3-pyridyl)-imidazole(finely pulverised) are added and 590 ml of water preheated to 40°C are emulsified in. The emulsion is stirred until it cools to room temperature and filled in tubes.

The following Examples illustrate in more detail the manufacture of the new imidazole derivatives of the general formula I, but without restricting the invention in any way. Temperatures are given in degrees centigrade.

EXAMPLE 1

2-tert.butyl-4(5)-(p-methoxyphenyl)-5(4)-(3-pyridyl)-imidazole a. p-methoxybenzyl-(3-pyridyl)-ketone The mixture of 56.6 g (0.375 mol) of nicotinic acid ethyl ester and 75.6 g (0.39 mol) of p-methoxyphenylacetic acid ethyl ester is treated under nitrogen in small amounts with 31.6 g (0.585 mol) of sodium methylate at 20°–25°C. The reaction mixture is stirred for 20 hours at 60°–70°C, in the process of which the alcohol which is formed is blown off with a weak flow of nitrogen. Then 118 ml of concentrated hydrochloric acid are added dropwise to the solid substance and the mixture is boiled for 3 hours under reflux. Upon cooling, the acid solution is washed with ether. The acid, aqueous phase is then adjusted to pH 5 with dilute ammonia and ice and made alkaline with sodium bicarbonate. The suspension is extracted with ethyl acetate. The organic phase is dried over sodium sulphate and evaporated to leave as residue the p-methoxybenzyl-(3-pyridyl)-ketone in the form of yellow crystals (m.p. 86°–87°C).

b. 1-(p-methoxyphenyl)-2-(3-pyridyl)-glyoxal

The mixture of 6.8 g (0.03 mol) of p-methoxybenzyl-(3-pyridyl)-ketone, 3.32 g (0.03 mol) of selenium dioxide and 80 ml of glacial acetic acid is boiled under reflux for 6 hours and subsequently filtered hot. The filtrate is evaporated in vacuo, the residue taken up in ethyl acetate and the solution filtered through a column filled with 240 g of silica gel. The filtrate is evaporated and the residue so obtained recrystallised from cyclohexane to yield 1-(p-methoxyphenyl)-2-(3-pyridyl)-glyoxal (m.p. 70°–72°C).

c. 2-tert.butyl-4(5)-)p-methoxyphenyl)-5(4)-(3-pyridyl)-imidazole

The mixture of 10.0 g (0.0415 mol) of 1-(p-methoxyphenyl)-2-(3-pyridyl)-glyoxal, 3.58 g (0.0415 mol) of pivalaldehyde, 20 g of ammonium acetate and 100 ml of glacial acetic acid is boiled under reflux for 22 hours and then, while stirring vigorously, poured into a mixture of 350 g of ice and 250 ml of concentrated ammonia solution. The crystal broth is extracted with ethyl acetate and the organic phase washed until neutral with sodium chloride solution, dried with sodium sulphate and evaporated. The residue is recrystallised from toluene and dried in a high vacuum at 120°C. The 2-tert.butyl-4(5)-(p-methoxyphenyl)-5(4)-(3-pyridyl)-imidazole is obtained in the form of white crystals (m.p. 202°–204°C).

The following compounds are manufactured by analogous methods:

2-isopropyl-4(5)-(p-methoxyphenyl)-5(4)-(3-pyridyl)-imidazole (m.p. 160°–162°C), starting from 10.0 g of the above diketone and 3.7 g of isobutyraldehyde:, 2-(p-chlorophenyl)-4(5)-(p-methoxyphenyl)-5(4)-(3-pyridyl)-imidazole (m.p. 200°–203°C), starting from 10.0 g of 1-(p-methoxyphenyl)-2-(3-pyridyl)-glyoxal and 6.5 g of p-chlorobenzaldehyde;

2-(p-chlorophenyl)-4(5)-phenyl-5(4)-(3-pyridyl)-imidazole (m.p. 206°–208°C), starting from 10.0 g of 1-phenyl-2-(3-pyridyl)-glyoxal and 6.7 g of p-chlorobenzaldehyde.

EXAMPLE 2

2-tert.butyl-4(5)-(o-chlorophenyl)-5(4)-(3-pyridyl)-imidazole a. o-chlorobenzyl-(3-pyridyl)-ketone The mixture of 25.0 g (0.126 mol) of o-chlorophenylacetic acid ethyl ester and 19.0 g (0.126 mol) of nicotinic acid ethyl ester is treated in small amounts under nitrogen with 10.2 g (0.196 mol) of sodium methylate at 20°–25°C. The reaction mixture is stirred for 20 hours at 60°–70°C, in the process of which the alcohol which is formed is blown off with a weak flow of nitrogen. After the dropwise addition of 40 ml of concentrated hydrochloric acid, the bath is boiled under reflux for 18 hours, then cooled and extracted with ether. The aqueous acid phase is adjusted to pH 5 with dilute ammonia solution and ice and made alkaline with sodium hydrogen carbonate solution. The resulting suspension is extracted with ethyl acetate. The organic phase is dried over sodium sulphate and evaporated, to yield yellow crystals of o-chlorobenzyl-(3-pyridyl)-ketone (m.p. 64°–67°C).

The following ketones are manufactured analogously:

o-xylyl-(3-pyridyl)-ketone (oil), starting from 21.0 g of o-tolylacetic acid ethyl ester and 17.8 g of nicotinic acid ethyl ester; m-xylyl-(3-pyridyl)-ketone (oil), starting from 21.0 g of m-tolylacetic acid ethyl ester and 17.8 g of nicotinic acid ethyl ester; p-xylyl-(3-pyridyl)-ketone, m.p. 90°–91°C (from ether), starting from 21.0 g of p-tolylacetic acid ethyl ester and 17.8 g of nicotinic acid ethyl ester; m-chlorobenzyl-(3-pyridyl)-ketone, m.p. 65°–67°C, starting from 25.0 g of m-chlorophenylacetic acid ethyl ester and 19.0 g of nicotinic acid ethyl ester; p-chlorobenzyl-(3-pyridyl)-ketone (oil), starting from 25.0 g of p-chlorophenylacetic acid ethyl ester and 19.0 g of nicotinic acid ethyl ester; p-methoxybenzyl-(4-pyridyl)-ketone, m.p. 130°–132°C, starting from 25.2 g of p-methoxyphenylacetic acid ethyl ester and 18.9 g of nicotinic acid ethyl ester; m-methoxybenzyl-(3-pyridyl)-ketone, b.p. 160°–165°C/0.05 Torr, starting from 25.2 g of m-methoxyphenylacetic acid ethyl ester and 19.0 g of nicotinic acid ethyl ester.

b. 1-(o-chlorophenyl)2-(3-pyridyl)-glyoxal

The mixture of 13.2 g (0.057 mol) of o-chlorobenzyl-(3-pyridyl)-ketone, 6.65 g (0.06 mol) of selenium dioxide and 50 ml of glacial acetic acid is boiled under reflux and subsequently filtered hot. The filtrate is evaporated in vacuo, the residue taken up in ethyl acetate and the solution filtered through a column filled with 450 g of silica gel. The filtrate is evaporated to leave as residue yellow crystals which melt at 50°–52°C and are used direct by for further processing.

The following glyoxals are manufactured analogously:

1-(p-chlorophenyl)-2-(3-pyridyl)-glyoxal, m.p. 80°–82°, starting from 13,2 g of chlorobenzyl-(3-pyridyl)-ketone and 6,65 g of selenium dioxide;

1-(m-chlorophenyl)-2-(3-pyridyl)-glyoxal, m.p. 55°–57°, starting from 13,2 g of m-chlorobenzyl-(3-pyridyl)-ketone and 6,65 g of selenium dioxide;

1-(o-tolyl)-2-(3-pyridyl)-glyoxal, b.p. 150°/0,01 Torr, starting from 42,0 g of o-xylyl-(3-pyridyl)-ketone and 24,0 g of selenium dioxide;

1-(m-tolyl)-2-(3-pyridyl)-glyoxal, b.p. 160°/0,05 Torr, starting from 28,0 g of m-xylyl-(3-pyridyl)-ketone and 16,0 g of selenium dioxide;

1-(p-tolyl)-2-(3-pyridyl)-glyoxal, m.p. 38°–40°, starting from 42,0 g of p-xylyl-(3-pyridyl)-ketone and 24,0 g of selenium dioxide;

1-(m-methoxyphenyl)-2-(3-pyridyl)-glyoxal, m.p. 48°–50°, starting from 4,9 g of m-methoxybenzyl-(3-pyridyl)-ketone and 2,6 g of selenium dioxide;

1-(p-methoxyphenyl)-2-(4-pyridyl)-glyoxal, m.p. 64°–65°, starting from 4,9 g of p-methoxybenzyl-(4-pyridyl)-ketone and 2,5 g of selenium dioxide.

c.
2-tert.butyl-4(5)-(o-chlorophenyl)-5(4)-(3-pyridyl)-imidazole

The mixture of 9.83 g (0.04 mol) of 1-(o-chlorophenyl)-2-(3-pyridyl)-glyoxal, 3.79 g (0.044 mol) of pivalaldehyde, 20 g of ammonium acetate and 100 ml of glacial acetic acid is boiled under reflux for 24 hours and then, while stirring vigorously, poured into a mixture of 350 g of ice and 250 ml of concentrated aqueous ammonia solution. The crystal broth is extracted with ethyl acetate and the organic phase washed until neutral saturated sodium chloride solution, dried with sodium sulphate and evaporated. The residue is recrystallised from toluene and dried in a high vacuum at 120°C to yield 2-tert.butyl-4-(5)-(o-chlorophenyl)-5-(4)-(3-pyridyl)-imidazole (m.p. 205°–206°C).

The following compounds are manufactured analogously:

2-tert.butyl-4(5)-(p-chlorophenyl)-5(4)-(3-pyridyl)-imidazole, m.p. 241° – 244°C, starting from 9,83 g of 1-(p-chlorophenyl)-2-(3-pyridyl)-glyoxal and 3,79 g of pivaldehyde;

2-tert.butyl-4(5)-(m-chlorophenyl)-5(4)-(3-pyridyl)-imidazole, m.p. 170° – 174°C, starting from 9,83 g of 1-(m-chlorophenyl)-2-(3-pyridyl)-glyoxal and 3,79 g of pivalaldehyde;

2-tert.butyl-4(5)-(o-tolyl)-5(4)-(3-pyridyl)-imidazole, m.p. 215° – 217°C, starting from 9,0 g of 1-(o-tolyl)-2-(3-pyridyl)-glyoxal and 3,79 g of pivalaldehyde;

2-tert.butyl-4(5)-(m-tolyl)-5(4)-(3-pyridyl)-imidazole, m.p. 170° – 171°C, starting from 9,0 g of 1-(m-tolyl)-2-(3-pyridyl)-glyoxal and 3,79 g of pivalaldehyde;

2-tert.butyl-4(5)-(p-tolyl)-5(4)-(3-pyridyl)-imidazole, m.p. 228° – 229°C, starting from 9,0 g of 1-(p-tolyl)-2-(3-pyridyl)-glyoxal and 3,79 g of pivalaldehyde;

2-(p-chlorophenyl)-4(5)-(m-tolyl)-5(4)-(3-pyridyl)-imidazole, m.p. 182° – 183°C, starting from 10,1 g of 1-(m-tolyl)-2-(3-pyridyl)-glyoxal and 6,4 g of p-chlorobenzaldehyde;

2-tert.butyl-4(5)-(m-methoxyphenyl)-5(4)-(3-pyridyl)-imidazole, m.p. 151° – 152°C, starting from 10,0 g of 1-(m-methoxyphenyl)-2-(3-pyridyl)-glyoxal and 3,6 g of pivalaldehyde;

2-tert.butyl-4(5)-(p-methylthio-phenyl)-5(4)-(3-pyridyl)-imidazole m.p. 199° – 200°C, starting from 11,0 g of 1-(p-methylthio-phenyl)-2-(3-pyridyl)-glyoxal and 3,64 g of pivalaldehyde.

EXAMPLE 3

2-tert.butyl-4(5)-phenyl-5(4)-(3-pyridyl)-imidazole

The mixture of 14.0 g (0.0664 mol) of 1-phenyl-2-(3-pyridyl)-glyoxal, 5.76 g (0.067 mol) of pivalaldehyde, 42 g of ammonium acetate and 110 ml of glacial acetic acid is boiled under reflux for 18 hours and, while stirring vigorously, subsequently poured into a mixture of 350 g of ice and 270 ml of concentrated aqueous ammonia solution. The crystal broth is extracted with ethyl acetate and the organic phase washed until neutral with saturated sodium chloride solution, dried with sodium sulphate and evaporated in a rotary evaporator. The residue is recrystallised from toluene and dried at 120°C in a high vacuum to yield 2-tert.butyl-4(5)-phenyl-5(4)-(3-pyridyl)-imidazole in the form of white crystals which melt at 188°–189°C.

The starting material is manufactured as follows:

a. benzyl-(3-pyridyl)-ketone

The mixture of 27.4 g (0.2 mol) of nicotinic acid methyl ester and 30 g (0.2 mol) of phenylacetic acid methyl ester is treated in small amounts under nitrogen with 16.2 g (0.3 mol) of sodium methylate at 20°–25°C. The reaction mixture is stirred for 20 hours at 60°–70°C, in the process of which the alcohol which is formed is blown off. Then 60 ml of concentrated hydrochloric acid is added dropwise to the solid substance and the mixture is boiled for 3 hours under reflux. The still hot yellow solution is treated with 30 ml of water and cooled to 50°C. Then 60 ml of chloroform are added and the reaction mixture is cooled to 5°C. The white crystals which form are collected by suction filtration and washed with chloroform; they melt at 225°C (from ethanol).

b. 1-phenyl-2-(3-pyridyl)-glyoxal 23.4 g (0.1 mol) of benzyl-(3-pyridyl)-ketone-hydrochloride are taken up in 180 ml of dimethyl sulphoxide and the solution is treated with 20 ml of 48% hydrobromic acid. The reaction mixture is stirred for 18 hours at 80° – 85°C and subsequently poured on a mixture of 800 g of ice and 1000 ml of water. The yellow emulsion is extracted with 2 × 200 ml of ethyl acetate. The two organic phases are combined, washed with water and dried over sodium sulphate. The red solution is concentrated in a rotary evaporator until a residual oil is left which is distilled in a bulb tube at 140° – 150°C/0.1 Torr (m.p. 56° – 57°C).

EXAMPLE 4

2-tert.butyl-4(5)-(p-methoxyphenyl)-5(4)-(4-pyridyl)-imidazole

The mixture of 3.7 g (0.015 mol) of 1-(p-methoxyphenyl)-2-(4-pyridyl)-glyoxal, 1.32 g (0.015 mol) of pivalaldehyde, 12 g of ammonium acetate and 40 ml of glacial acetic acid is boiled under reflux for 13 hours and then, while stirring vigorously, poured into a mixture of 120 g of ice and 100 ml of concentrated aqueous ammonium solution. The crystal broth is extracted with ethyl acetate and the organic phase is washed until neutral with saturated sodium chloride solution, dried with sodium sulphate and evaporated in a rotary evaporator. The residue is recrystallised from toluene and dried in a high vacuum at 120°C to yield 2-tert.butyl-4(5)-(p-methoxyphenyl)-5(4)-(4-pyridyl)-imidazole in the form of white crystals which melt at 258°–260°C.

The following compounds are manufactured analogously:

2-tert.butyl-4(5)-phenyl-5(4)-(4-pyridyl)-imidazole (m.p. 266° – 268°C), starting from 3.2 g of 1-phenyl-2-(4-pyridyl)-glyoxal and 1.3 g of pivalaldehyde;

2-(p-chlorophenyl)-4(5)-(p-methoxyphenyl)-5(4)-(4-pyridyl)-imidazole (m.p. 286° – 288°C), starting from 7.0 g of 1-(p-methoxyphenyl)-2-(4-pyridyl)-glyoxal and 4.2 g of p-chlorobenzaldehyde.

EXAMPLE 5

2-tert.butyl-4(5)-(p-methoxyphenyl)-5(4)-(2-pyridyl)-imidazole a. 1-(p-methoxyphenyl)-2-(2-pyridyl)-glyoxal 30 g (0.142 mol) of 2-(4'-methoxy-styryl)-pyridine are treated in small amounts at 200°C and within 30 minutes with 34.5 g (0.31 mol) of selenium dioxide. The reaction mixture is kept for a further 30 minutes at about 200°C and then cooled to 50°C. The warm residue is taken up in 250 ml of methylene chloride and the solution is filtered through a chromatography column containing 1000 g of silica gel. Yellow crystals are obtained (m.p. 97° – 98°C).

b. 2-tert.butyl-4(5)-(p-methoxyphenyl)-5(4)-(2-pyridyl)-imidazole 7.2 g (0.03 mol) of 1-(p-methoxyphenyl)-2-(2-pyridyl)-glyoxal are boiled under reflux for 18 hours together with 2.6 g (0.03 mol) of pivalaldehyde, 16 g of ammonium acetate and 70 ml of glacial acetic acid and, while stirring vigorously, the mixture is then poured into a mixture of 220 g of ice and 190 ml of concentrated ammonia solution. The crystal broth is extracted with ethyl acetate and the organic phase is washed until neutral with saturated sodium chloride solution, dried with sodium sulphate and evaporated in a rotary evaporator. The residue is recrystallised from cyclohexane and dried in a high vacuum at 110°C to yield the 2-tert.butyl-4(5)-(p-methoxyphenyl)-5(4)-(2-pyridyl)-imidazole in the form of white crystals which melt at 139° – 140°C.

The following compounds are manufactured analogously:

2-phenyl-4(5)-(p-methoxyphenyl)-5(4)-(2-pyridyl)-imidazole (m.p. 207° – 208°C), starting from 2.5 g of the above diketone and 1,1 g of benzaldehyde;

2-(p-chlorophenyl)-4(5)-(p-methoxyphenyl)-5(4)-(2-pyridyl)-imidazole (m.p. 219° – 220°C) starting from 6.0 g of the above diketone and 3.5 g of p-chlorobenzaldehyde;

2-tert.butyl-4(5)-phenyl-5(4)-(2-pyridyl)-imidazole (m.p. 162° – 164°C), starting from 12.0 g of 1-phenyl-2-(2-pyridyl)-glyoxal and 4.9 g of pivalaldehyde.

EXAMPLE 6

2-tert.butyl-4(5)-phenyl-5(4)-(3-pyridyl)-imidazole 38.4 g (0.18 mol) of α-hydroxybenzyl-3-pyridyl ketone (manufactured according to J. Chem. Soc. 1956, 2913) are dissolved with heating in 750 ml of methanol. At 30° to 35°C, 36.6 g (0.18 mol) of copper(II)-acetate-monohydrate are added, and then 17.2 g (0.20 mol) of pivalaldehyde. Within 10 minutes, 375 ml of concentrated ammonia solution are then added dropwise, and the solution is then boiled for 3 hours under reflux and filtered hot. The copper salt of the desired imidazole obtained as filter product is washed with 2 × 50 ml of hot methanol and subsequently suspended in 1000 ml of 80% ethanol. The ethanolic suspension is saturated with hydrogen sulphide at 80°C. After being stirred for 3 hours at 80°C, the hot suspension is filtered with suction to remove the copper sulphide. The filtrate is evaporated, the residue recrystallised from toluene and dried in a high vacuum at 120°C. The resulting 2-tert.butyl-4(5)-phenyl-5(4)-(3-pyridyl)-imidazole melts at 188° – 189°C.

EXAMPLE 7

5.6 g (0.020 mol) of N-[α-(3-pyridyl-carbonyl)-benzyl]-pivalamide are boiled for 14 hours under reflux with 13.1 g (0.17 mol) of ammonium acetate in 60 ml of glacial acetic acid. The brown solution is then poured on 120 ml of 120 ml of concentrated ammonia and 120 g of ice and the whole mixture is extracted with ethyl acetate. The organic phase is isolated, washed until neutral with saturated sodium chloride solution, dried over sodium sulphate and evaporated. The residue is crystallised from ethyl acetate to yield 2-tert.butyl-4(5)-phenyl-5(4)-(3-pyridyl)-imidazole which melts at 188° – 189°C.

EXAMPLE 8

2-tert.butyl-4(5)-phenyl-5(4)-(2-pyridyl)-imidazole 4.10 g (0.03 mol) of pivalamidine hydrochloride in 15 ml of water are added to a solution of 6.90 g (0.025 mol) of 2-(α-bromo-phenacyl)-pyridine (manufactured according to B. Eistert and E. Endres, Ann. 734, 56 – 69 (1970)) in 40 ml of chloroform. While stirring vigorously and introducing nitrogen, the amulsion is treated dropwise at 15° – 20°C with the solution of 2.9 g (0.06 mol) of potassium hydroxide in 15 ml of water, the bath boiled for 4½ hours under reflux and, while still hot, poured into a separating funnel. The lower organic phase is isolated, washed with 2N sodium carbonate solution and saturated sodium chloride solution, dried over sodium sulphate and evaporated. The residue is recrystallised from toluene and dried in a high vacuum at 120°C to yield the 2-tert.butyl-4(5)-phenyl-5(4)-(2-pyridyl)-imidazole which melts at 162° – 164°C.

The following compound is obtained analogously: 2-tert.butyl-4(5)-phenyl-5(4)-(3-pyridyl)-imidazole (m.p. 188°–189°C), starting from 6.9 g of 3-(α-bromophenacyl)-pyridine and 4.1 g of pivalamidine hydrochloride.

EXAMPLE 9 a. (α-hydroxyimino-benzyl)-(3-pyridyl)-ketone 9.8 g (0.05 mol) of benzyl-(3-pyridyl)-ketone are dissolved in 250 ml of ethanol and 88 ml of 2N hydrochloric acid. A solution of 7.0 g of sodium nitrite in 100 ml of water is added dropwise at 20° – 25°C within 20 minutes. The reaction mixture is stirred for 15 hours at 20° – 25°C and subsequently made alkaline with 2N sodium hydrogen carbonate solution. Then 1000 ml of water are added and the mixture is filtered with suction. The filter product is recrystallised from alcohol (m.p. 169° – 172°C).

The following compound is manufactured analogously: (α-hydroximino-p-methoxybenzyl)-(3-pyridyl)-ketone (m.p. 183°–186°C), starting from 11.3 g (p-methoxybenzyl)-(3-pyridyl)-ketone.

b. 2-tert.butyl-4-phenyl-5-(3-pyridyl)-imidazole-3-oxide

The mixture of 11.3 g (0.05 mol) of (α-hydroximinobenzyl)-(3-pyridyl)-ketone (m.p. 169° – 172°C), 5.3 g (0.05 mol) of pivalaldehyde, 10 g of ammonium acetate and 50 ml of glacial acetic acid is boiled under reflux for 3 hours. The still hot solution is poured on ice and made alkaline with concentrated ammonia solution. The crystal broth is extracted with ethyl acetate. The organic phase is washed until neutral, dried over sodium sulphate and evaporated. The residue is recrystallised from ethyl acetate and dried in a high vacuum at 150°C (m.p. 247° – 248°C).

The following compound is obtained analogously: 2-tert.butyl-4-(p-methoxyphenyl)-5(3-pyridyl)-imidazole-3-oxide (m.p. 245° – 247°C), starting from 12.8 g of (α-hydroximino-p-methoxy-benzyl)-(3-pyridyl)-ketone.

c. 2-tert.butyl-4-(5)-phenyl-5(4)-(3-pyridyl)-imidazole

A solution of 5.0 g of 2-tert.butyl-4-phenyl-5-(3-pyridyl)-imidazole-3-oxide in 30 ml of chloroform is treated dropwise, while cooling with ice, with 6.5 ml of phosphorus trichloride and the mixture is subsequently stirred for 2 hours at 100°C. After the reaction mixture has cooled, it is treated with 20 ml of water and adjusted to pH 7.5 with dilute ammonia. The mixture is extracted with ethyl acetate. The ethyl acetate solution is washed in saturated sodium chloride solution, dried over sodium sulphate and evaporated under 11 Torr. The residue is crystallised from toluene. The 2-tert.butyl-4(5)-phenyl-5(4)-(3-pyridyl)-imidazole melts at 188° – 189°C after being dried in a high vacuum at 120°C.

The following compound is obtained analogously: 2-tert.butyl-4-(p-methoxyphenyl)-5-(3-pyridyl)-imidazole (m.p. 202° – 204°C), starting from 2-tert.butyl-4-(p-methoxyphenyl)-5-(3-pyridyl)-imidazole-3-oxide.

EXAMPLE 10 a. benzyl-[3-(pyridyl-1-oxide)]-ketone

A mixture of 31.2 g of nicotinic acid ethyl ester-N-oxide (0.19 mol) and 31 ml of phenylacetic acid ethyl ester (0.195 mol) is treated in small amounts under nitrogen with 15.8 g of sodium methylate (0.291 mol). The mixture is stirred for 1 hour at 20°C and then for 20 hours at 60° – 70°C, in the course of which the alcohol which forms is removed by the nitrogen which is passed in. The mixture is cooled to room temperature, treated with 60 ml of concentrated hydrochloric acid and boiled under reflux for 3 hours. The batch is then cooled to room temperature, 40 ml of water are added, the dark solution is extracted with 2 × 50 ml of chloroform and adjusted to pH 5 with dilute ammonia and ice. Then 2N sodium carbonate solution is added until the reaction turns alkaline and the aqueous solution is extracted with saturated sodium chloride solution. The ethyl acetate solution is washed with saturated sodium chloride solution, dried over sodium sulphate and evaporated at 40°C under 11 Torr. The benzyl-[3-(pyridyl-1-oxide)]-ketone melts at 123° – 125°C.

b. 1-phenyl-2-[3-(pyridyl-1-oxide)]-glyoxal

A mixture of 8.2 g of benzyl-[3-(pyridyl-1-oxide)]-ketone (0.0385 mol), 5.0 g of selenium dioxide and 50 ml of glacial acetic acid is boiled for 6 hours under reflux, filtered hot and treated with 5000 ml of water. The mixture is extracted with ethyl acetate, the ethyl acetate solution washed with saturated sodium chloride solution, dried over sodium sulphate and evaporated at 40°C under 11 Torr. To yield the 1-benzyl-2-[3-(pyridyl-1-oxide)]-glyoxal in the form of an oil.

c.
2-tert.butyl-4(5)-phenyl-5(4)-[3-pyridyl-1-oxide)]-imidazole

A mixture of 9.5 g of 1-phenyl-2-[3-(pyridyl-1-oxide)]-glyoxal (0.042 mol), 4.6 ml of pivalaldehyde, 20.0 g of ammonium acetate and 150 ml of glacial acetic acid is boiled for 5 hours under reflux, then cooled and poured into a mixture of 3000 g of ice and 200 ml of concentrated aqueous ammonia solution. The mixture is extracted with ethyl acetate and the ethyl acetate solution washed with saturated sodium chloride solution, dried over sodium sulphate and evaporated under 11 Torr, to yield the 2-tert.butyl-4(5)-phenyl-5(4)-[3-(pyridyl-1-oxide)]-imidazole.

d. 2-tert.butyl-4(5)-phenyl-5(4)-(3-pyridyl)-imidazole

Using 2-tert.butyl-4(5)-phenyl-5(4)-[3-pyridyl-1-oxide)]-imidazole as starting material, the above compound (m.p. 188° – 189°C) is obtained by a method analogous to that described in Example 9 c).

EXAMPLE 11

A solution of 27.8 g (0.10 mol) of 2-tert.butyl-4(5)-phenyl-5(4)-(3-pyridyl)-imidazole in 900 ml of acetone is treated at 20° – 25°C with 9.61 g (6.5 ml, 0.10 mol) of methanesulphonic acid and the reaction mixture is then stirred for about 15 hours. The white crystals which form are collected by suction filtration. The 3-tert.butyl-4(5)-phenyl-5(4)-(3-pyridyl)-imidazole-methanesulphonate obtained after recrystallisation from ethanol/ether melts at 238° – 240°C.

EXAMPLE 12 a. phenyl-(pyrazinyl-2-methyl)-ketone 37.6 g of 2-methylpyrazine (0.4 mol) are added dropwise at −40°C and over the course of 20 minutes to a sodium amide solution prepared from 9.2 g of sodium (0.4 mol), 0.1 g of ferric chloride and 300 ml of liquid ammonia. The red solution is stirred for 2 hours at −40°C and then a solution of 27.2 g of benzoic acid methyl ester (0.2 mol) in 30 ml of absolute ether is added dropwise within 20 minutes at −40°C. The mixture is stirred for 1 hour at −40°C and subsequently treated in small amounts with 25.0 g of ammonium chloride and 250 ml of absolute ether. The ammonia is evaporated off at −20°C and after 2 hours a further amount of 150 ml of absolute ether is added. The batch is stirred for 1 hour at room temperature and the phenyl-(pyrazinyl-2-methyl)-ketone crystallises from the ether solution. The ketone is recrystallised from ethanol and melts at 97° – 100°C. The following compound is obtained analogously: p-methoxyphenyl-(pyrazinyl-2-methyl)-ketone (m.p. 77° – 85°C), starting from 27.6 g of 2-methyl-pyrazine and 34.2 g of anisic acid methyl ester.

b. 1-phenyl-2-(2-pyrazinyl)-glyoxal

A mixture of 7.2 g of phenyl-(pyrazinyl-2-methyl)-ketone, 6.1 g of selenium dioxide and 80 ml of absolute dioxan is heated to the boil under reflux for 6 hours and then filtered. The filter product is thoroughly washed with dioxan and the combined filtrates are evaporated under 11 Torr. The residual oil is dissolved in 100 ml of chloroform. The chloroform solution is shaken with florosil and filtered off. The filtrate is concentrated under 11 Torr and the residue distilled in a bulb tube. The 1-phenyl-2-(2-pyrazinyl)-glyoxal boils at 170°–180°C/0.05 Torr.

The following compound is obtained analogously:
1-(p-methoxyphenyl)-2-(2-pyrazinyl)-glyoxal, b.p. 190° – 210°C/0.001 Torr, starting from 10.0 g of methoxyphenyl-(pyrazinyl-2-methyl)-ketone.

c.
2-tert.butyl-4(5)-(2-pyrazinyl)-5(4)-phenyl-imidazole

A mixture of 4.7 g of 1-phenyl-2-(2-pyrazinyl)-glyoxal, 2.9 ml of pivalaldehyde, 15.0 g of ammonium acetate and 50 ml of glacial acetic acid is heated to the boil under reflux for 2 hours and then, while stirring thoroughly, poured into a mixture of 170 g of ice and 120 ml of concentrated aqueous ammonia solution. The precipitated crystal broth is extracted with ethyl acetate. The ethyl acetate extract is washed with saturated sodium chloride solution, dried over sodium sulphate and evaporated at 40°C under 11 Torr. The residue is crystallised from toluene. The 2-tert.butyl-4(5)-(2-pyrazinyl)-5(4)-phenyl-imidazole melts at 153° – 156°C.

The following compound is obtained analogously:
2-tert.butyl-4(5)-(2-pyrazinyl)-5(4)-(p-methoxyphenyl)-imidazole (m.p. 161° – 163°C), starting from 6.5 g of 1-(p-methoxyphenyl)-2-(2-pyrazinyl)-glyoxal.

EXAMPLE 13 a. (p-methylthiobenzyl)-(3-pyridyl)-ketone

A mixture of 14.6 g of nicotonic acid ethyl ester and 19.5 g of p-methylthiophenylacetic acid ethyl ester is treated in small amounts with 9.4 g of sodium methylate. The mixture is then stirred for 1 hour at 20°C and subsequently for 4 hours at 65°C. Then 40 ml of concentrated hydrochloric acid are added and the suspension is heated for 7 hours to the boil under reflux, cooled, and after addition of 40 ml of water, extracted with ethyl acetate. The ethyl acetate solution is extracted with 2N hydrochloric acid, the hydrochloric acid extract made alkaline with 2N sodium carbonate solution, and the suspension is extracted with ethyl acetate. The ethyl acetate solution is washed with saturated sodium chloride solution, dried over sodium sulphate and evaporated under 11 Torr. The residue is crystallised from ethyl acetate/petroleum ether. The (p-methylthiobenzyl)-(3-pyridyl)-ketone melts at 125° – 127°C.

b. (p-methylsulphonylbenzyl)-(3-pyridyl)-ketone

A mixture of 5.0 g of (p-methylthiobenzyl)-(3-pyridyl)-ketone, 10 ml of 30% hydrogen peroxide and 100 ml of glacial acetic acid is stirred for 10 hours at room temperature and then poured on 4000 ml of ice. The mixture is extracted with ethyl acetate. The ethyl acetate solution is washed with saturated sodium chloride solution, dried over sodium sulphate and evaporated at 40°C under 11 Torr. The residue is crystallised from ethanol. The (p-methylsulphonylbenzyl)-(3-pyridyl)-ketone melts at 146° – 148°C.

c. 1-(p-methylsulphonylphenyl)-2-(3-pyridyl)-glyoxal

The mixture of 27.0 g of (p-methylsulphonylbenzyl)-3-pyridyl)-ketone, 11.1 g of selenium dioxide and 5000 ml of glacial acetic acid is heated to the boil for 8 hours under reflux and filtered through hyflo. The filtrate is diluted with 3000 ml of water and adjusted to pH 6–7 with ammonia. After extraction with ethyl acetate, the ethyl acetate solution is washed with saturated sodium chloride solution, dried over sodium sulphate and concentrated at 40°C under 11 Torr. The yellow crystalline residue is crystallised from toluene. The 1-(p-methylsulphonylphenyl)-2-(3-pyridyl)-glyoxal melts at 160°–170°C.

d. 2-tert.butyl-4(5)-(p-methylsulphonylphenyl)-5(4)-(3-pyridyl)-imidazole

A mixture of 9.0 g of 1-(p-methylsulphonylphenyl)-2-(3-pyridyl)-glyoxal, 3.5 ml of pivalaldehyde, 20.0 g of ammonium acetate and 200 ml of glacial acetic acid is heated to the boil under reflux for 5 hours and then poured into a mixture of 300 ml of ice and 200 ml of concentrated aqueous ammonia solution. The suspension is extracted with ethyl acetate. The ethyl acetate solution is then washed with saturated sodium chloride solution, dried over sodium sulphate and evaporated under 11 Torr. The residue is chromatographed on 200 g of silica gel. The fractions 5 and 6, each eluted with 250 ml of ethyl acetate, contain the 2-tert.butyl-4(5)-(p-methylsulphonylphenyl)-5(4)-(3-pyridyl)-imidazole, which melts at 120°–125°C (from toluene).

I claim:

1. A pharmaceutical composition for treating pain in mammals comprising an effective amount of a compound of the formula

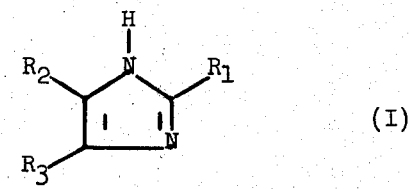

(I)

wherein $R_1$ represents isopropyl, sec.butyl, tert.butyl or p-chlorophenyl, one of the groups $R_2$ and $R_3$ represents a phenyl group or a p-methoxyphenyl, and the other represents a pyridyl group, or a pharmaceutically acceptable acid addition salt thereof and a pharmaceutical carrier.

2. A method of treating pain in mammals which comprises administering to said mammals an effective amount of a compound according to claim 1.

* * * * *